(12) United States Patent
Patel

(10) Patent No.: US 10,006,868 B2
(45) Date of Patent: Jun. 26, 2018

(54) METHOD AND DEVICE FOR GEMSTONE EVOLUTION

(71) Applicant: Arvindbhai Lavjibhai Patel, Ahmedabad (IN)

(72) Inventor: Arvindbhai Lavjibhai Patel, Ahmedabad (IN)

( * ) Notice: Subject to any disclaimer, the term of this patent is extended or adjusted under 35 U.S.C. 154(b) by 227 days.

(21) Appl. No.: 14/899,586

(22) PCT Filed: Sep. 11, 2013

(86) PCT No.: PCT/IN2013/000550
§ 371 (c)(1),
(2) Date: Dec. 18, 2015

(87) PCT Pub. No.: WO2014/203266
PCT Pub. Date: Dec. 24, 2014

(65) Prior Publication Data
US 2016/0139058 A1    May 19, 2016

(30) Foreign Application Priority Data
Jun. 18, 2013    (IN) .......................... 2069/MUM/2013

(51) Int. Cl.
*G01N 21/87*   (2006.01)
*G01N 1/34*    (2006.01)

(52) U.S. Cl.
CPC ............... *G01N 21/87* (2013.01); *G01N 1/34* (2013.01); *G01N 2201/025* (2013.01); *G01N 2201/06113* (2013.01)

(58) Field of Classification Search
USPC .......................................................... 356/30
See application file for complete search history.

(56) References Cited

U.S. PATENT DOCUMENTS

| | | | | |
|---|---|---|---|---|
| 3,673,412 A | * | 6/1972 | Olson | G02B 27/40 250/201.4 |
| 6,020,954 A | * | 2/2000 | Aggarwal | G01N 21/87 356/30 |
| 6,980,283 B1 | * | 12/2005 | Aggarwal | G01N 21/87 356/30 |
| 7,324,188 B1 | | 1/2008 | Beesley | |
| 2003/0110844 A1 | * | 6/2003 | Struckmeier | G01Q 60/42 73/105 |

(Continued)

FOREIGN PATENT DOCUMENTS

| | | |
|---|---|---|
| CN | 1518491 A | 8/2004 |
| CN | 101292152 A | 10/2008 |
| CN | 101652654 A | 2/2010 |

(Continued)

Primary Examiner — Tarifur Chowdhury
Assistant Examiner — Omar Nixon

(57) ABSTRACT

The present invention relates to the method and device to determination of the properties of gemstones and more particularly evolution of gemstone by detection of internal and external structure of gemstone. In particular, the present invention methods and device is used to identify the size, location of impurities/defects in raw gemstone with the help of optimize spectroscopy scanning. The present invention method and device is used for precise automatic evolution of gemstones and possibilities (estimation) of final value of planned gemstone after remaining gemstone processing cycle.

12 Claims, 2 Drawing Sheets

(56) References Cited

U.S. PATENT DOCUMENTS

Figure 1:
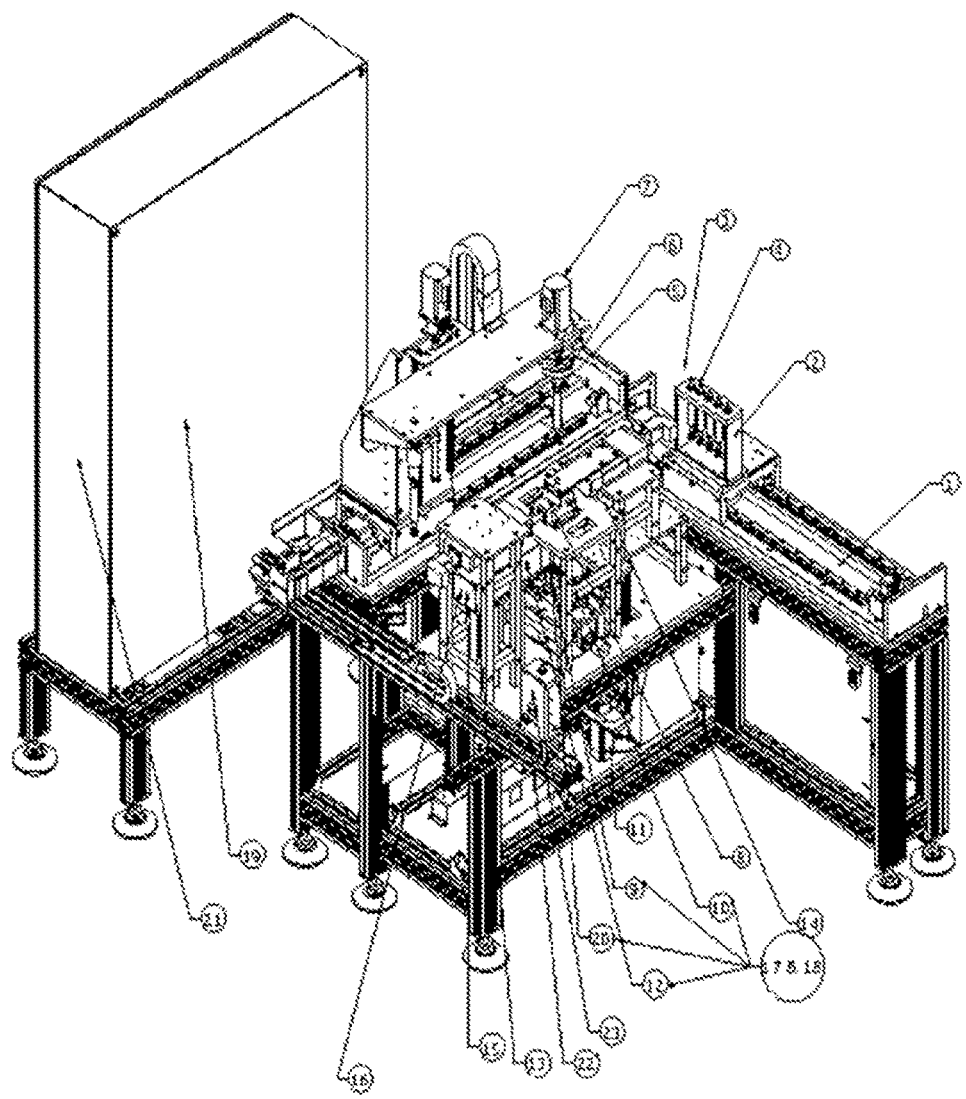

2008/0043220 A1* 2/2008 Kaplan ................ B23K 26/032
 356/30
2012/0268728 A1* 10/2012 Wagner ................ G01N 21/87
 356/30

FOREIGN PATENT DOCUMENTS

CN 102713582 A 10/2012
WO WO 12006054154 A1 5/2006

* cited by examiner

METHOD AND DEVICE FOR GEMSTONE EVOLUTION

FIELD OF THE INVENTION

The present invention relates to the method and device to determination of the properties of gemstones and more particularly evolution of gemstone by detection of internal and external structure of gemstone. In particular, the present invention methods and device is used to identify the size, location of impurities/defects in raw gemstone with the help of optimize spectroscopy scanning. The present invention method and device is used for precise automatic evolution of gemstones and possibilities (estimation) of final value of planned gemstone after remaining gemstone processing cycle.

BACKGROUND OF THE INVENTION

Diamond is a mineral composed of pure carbon. It is the hardest naturally occurring substance and popular gemstone. Because of extreme hardness, diamonds have a number of important industrial application. Diamond is a special form of Carbon like Graphite. In the mine, a raw diamond looks like a piece of coal—natural stone. Jewellery grade diamond cutting is a separate and special branch involves marking, cleaving, kerfing, blocking, sawing, bruiting, faceting and polishing.

Inside the raw stone there can be some impurities. The impurities inside the diamond are called NATS and GERUMS. Nats are impurities in the form of particles other then carbon and Gerums are the impurities in the form of micro-cracks in the stone. So, these impurities have to be removed from the stone, and that is why the raw stone is cut in such a way, that the maximum carat weight (volume) can be gained.

Before cutting the raw stone it is planned in the mind by imagination from where to cut to yield the desired value and size. Marking is done on the stone for cutting accordingly. To make this decision, the shape of rough diamond and the number and location of impurities is required to be considered as it affects reflectivity and clarity of the diamond. But the human imagination of the mankind can not judge the proper place of the impurities and it may have error and cutting is done randomly, so there may be lots of wastage. While cutting the stone there are permutation and combination in the form of size and numbers from one stone. When the cutting is done according to the human imagination, the desired proportion of and numbers can not be obtained and there may be a heavy loss.

Gemstone is used as ornamental objects, so, it is valued by their appearance rather than for industrial use. Particularly Gemstone value is calculated base up on the clarity, color, cut and carat. Color generally refers to the diamonds hue, and is related to impurities in the diamond's composition. Clarity generally refers to defects, such as bulk or surface defects, which can scatter light and reduce a diamond's visual appeal. The cut generally refers to both the diamond's shape (e.g., round, marquise, oval, etc.), and also to the diamond's proportions, symmetry, and polish. These parameters influence how light interacts with the diamond, which facets appear bright to an observer, which facets appear dark, and which facets appear colored.

The impurities inside the diamond are called NATS and GERUMS. Nats are impurities in the form of particles other then carbon and Gerums are the impurities in the form of micro-cracks in the stone. So, these impurities have to be removed from the stone, and that is why the raw stone is cut in such a way that the maximum carat weight (volume) can be gained.

In general practice, gemstone is evaluated by naked eye and optical magnifying glass by experienced skilled persons. They do their experienced efforts to identify internal defects and inclusions. By conventional method they always take care of planning as per their individual decision.

Optionally, gemstone are also evaluated by microscopic systems by experts and it was become little more accurate decision but still completely dependent on visual accuracy and manual inconsistency. However, diamond (gemstone) has very high refraction index and it creates lot of refractions and some total internal reflections due to light angle and uneven shape of rough stone. These all are limitations of the jewelry industry to detect real and precise size and position of inclusions (information) to create better planning and get maximum gain.

U.S. Pat. No. 4,259,011 describes how to identify the presence of inclusions but not their location. European patent 1,211,503, presents a possible solution for the locating of inclusions in a transparent and at least partially polished diamond by imaging the diamond twice and analyzing the images by computer so as to localize an inclusion with respect to the outer surface of the diamond. Although this patent makes reference to a refractive index correction factor to be included in the computer's calculations, it does not provide a solution to multiple images produced by a single inclusion.

U.S. Pat. No. 4,049,350 teaches eliminating the refractions and reflections at the facets of a cut stone by submerging the stone in a solution of similar refraction index. It describes how to locate an inclusion in a two dimensional plane by aiming a narrow laser beam at a preferred angle to a particular facet.

U.S. Pat. No. 4,152,069 also teaches submerging a cut stone in such a solution and how to find the inclusion within a three dimensional volume.

Both latter references do not disclose any information on the medium they used to closely match the refraction index of the gem, this being particularly problematic for diamonds that have a very high refraction index. In some conventional gemstone evolution method hazardous chemicals are used as medium, but during the diamond evolution or scanning method toxic gas in generated. To overcome above stated limitation and to evaluate gemstone more prosaically at microscopic level, the present invention method and device is used.

SUMMARY OF THE INVENTION

The invention relates to methods for grading gemstones, apparatus for grading gemstones, and systems that utilize such methods and apparatus.

Grades can be used to establish the commercial value of gemstones. One important aspect of embodiments of present invention relates to a best mathematical method with algorithm to make a decision of best possibilities of sawing planes in a 3D solid image of rough diamond to get maximum possible gain. In a detail explanation of embodiment of invention, to scan the rough diamond to get total external surface geometry and information.

The next process to mark some references to match at the time of internal structure close loop scanning system. Hyper Spectral Spectroscopy of rough diamond (gemstone) in suitable very precise optical medium with spectroscopic vision system and tunable spectroscopic light source is a key embodiment of invention. In a supreme embodiment of invention, hyper spectral spectroscopy with close loop scientific control system—development process of precise optical medium in best suitable environment which can match with phase velocity and optical properties of diamond. Spectroscopic vision system is a telescopic optical system designed and integrated from high transmission in applicable near Infra Red (IR) wavelength optics and high resolution photoelectric Near-infrared spectroscopy (NIRS) sensor. Wavelength tunable spectroscopic light source/narrow band collimated source/narrow band fine tuned laser is basically Visible and NIR photonics source designed and integrated from advanced NIR collimator optics and wavelength optics. It can be controlled and tuned by close loop control system to achieve exact matching of phase velocity, wavelength transmission and optical properties of diamond and optical media. Development process of precise optical medium is scientific process to prepare high refractive index media in absence of oxygen and presence of noble gas by heating Selenium. The tuning of temperature and wavelength are important aspects of advanced feedback related close loop system to match phase velocity and refractive index of optical media and diamond. The light transmission from clear portion of diamond and absorption from inclusions portions of diamond is key feedback for close loop system in this hyper spectroscopic mechanism. In a key embodiment of application oriented innovation, Photonics radiation based temperature control system—a scientific method of photonic energy absorption and conversion in heat to increase temperature and its control mechanism. This close loop system is to develop optical media of spectroscopy and to keep optical properties as it is for long time. The tunable photonics source/narrow band collimated source/laser can be controlled and illuminates in between wavelength band 350 nm to 2800 nm. At the scanning process of the total system, diamond (gemstone) is completely surrounded by developed optical media to detect precise location of inclusions. Integration of Optical Coherent Tomography (OCT) in combination with Hyper Spectral Spectroscopy—a method to get more information of rough diamond (gemstone) in image format with reference to different applicable wavelengths and image processing on multiple images to create detailed final internal structure of rough diamond (gemstone). Key embodiment of system, Industrial Automation System for total related process. This system contains stirring, ultrasonic surface treatment with cleaning, drying with hot clean air, store in positional stand rack, pick up holding part with diamond, execution of scanning in hyper spectral spectroscopy system and placing in stand rack. Present system relates to precise motion control mechanism, pick and place mechanism with preprogrammed sequence to provide better safety and reliability with great efficiency and manless operation

OBJECT OF THE INVENTION

In the present invention, raw diamond is scanned through the internal surface of the gemstone, which also locates the impurities/defects at microscopic level so, the evaluation method is fully automatic and more precise compared to existing gemstone evolution method and device.

The further object of the present invention, in the present evaluation method optimize spectroscopy method is used to locates the impurities/defects in the ram gemstone without any hazards chemicals so, the present invention is very eco friendly method of gemstone evolution.

An aspect of some representation of this invention relates to finding the size and positions of inclusions inside the diamond (gemstone) which has irregular or uneven shape called rough stone. It's also an aspect of creation of 3D reconstruction of rough stone including to total positional information of inclusions.

Hyper spectral spectroscopy with close loop scientific control system—development process of precise optical medium in best suitable environment with tuning of temperature and wavelength which can match with phase velocity and optical properties of diamond.

Integration of Optical Coherent Tomography—a method to get more information of rough diamond (gemstone) in image format with reference to different applicable wavelengths.

Photonics radiation based temperature control system—a scientific method of photonic energy absorption and conversion in heat to increase temperature and its control mechanism.

Industrial Automation System—contains stirring, ultrasonic surface treatment with cleaning, drying with hot clean air, store in positional stand rack, pick up holding part with diamond, execution of scanning in hyper spectral spectroscopy system and placing in stand rack.

DETAILED DESCRIPTION

The present invention is described in more details clearly with reference to following figures, which illustrates a preferred embodiment of the present invention and wherein, FIG. 1 represents the internal assembly of the present invention device.

Figure 2:
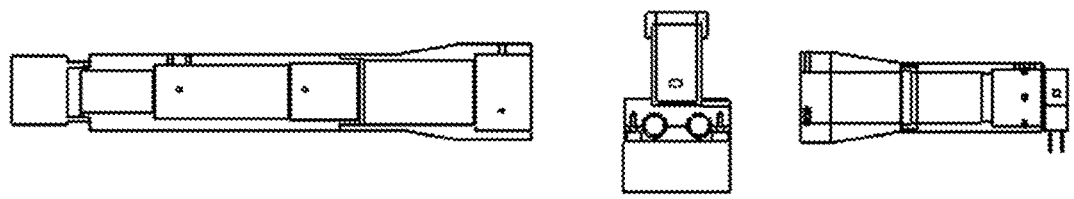

FIG. 2 represents the side view of diamond holder mechanism

Figure 3:
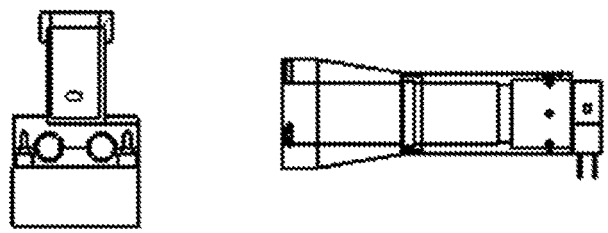
Figure 4:
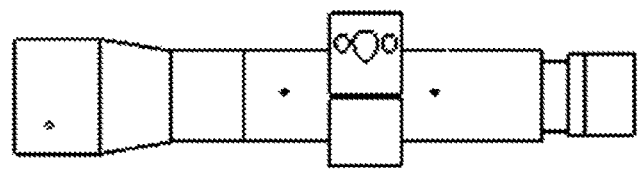

FIG. 3 represents the prospective view of adjustable diamond holder mechanism holding with rough diamond FIG. 4 represents the side view of hyper spectral spectroscopy with close loop system Exemplary embodiments of the invention are discussed in detail below while specific exemplary embodiments are discussed, it should be understood that this is done for illustration purpose only. A person skilled in the relevant art will recognize that other components and configuration can be used without parting from the spirit and scope of the invention.

DETAILS DESCRIPTION OF DRAWINGS

An aspect of some representation of this invention relates to finding the size and positions of inclusions inside the diamond (gemstone) which has irregular or uneven shape called rough stone. It's also an aspect of creation of 3D reconstruction of rough stone including to total positional information of inclusions.

In the FIG. 1, internal assembly of the present invented device is describing in the entire diamond evolution method. First the diamond holding die/fixture with gemstone is put at the entry tray track (1) for the evaluation.

In the entry tray (2), the mechanical device fixture applicable to set diamond holding die with gemstone to evaluate in hyper spectral spectroscopic system. Pick position system (3) is provided for automation system at entry tray to install. Diamond (Gemstone) holding die/fixture (4) is provided for easy to set and hold the diamond to keep process of hyper spectral spectroscopy. Pick assembly mechanism (5) mechatronics mechanism with automation which can pick the die and take at predefined position. Rotation assembly for spectroscopic analysis (6) is well developed precise mechanism to rotate the diamond holding die for hyper spectral spectroscopy and optical coherent tomography. A motor with built in torque sensing mechanism (7) which can help to get information of optical media's present situation. Die/fixture cleaning chamber (8) in which neutral or nobel gas will flow to clean the gemstone and also in absence of air particles. Optical media development chamber (9) in which in absence of air particles and in presence of neutral or nobel gas with close loop temperature control mechanism optical media will form for better performance of hyper spectral spectroscopy and optical coherent tomography. Radiation heat source or Photonics laser source (10), a electro optical heat source which can capable to heat optical media in radiation form. It can be a photonics laser source to provide heat on optical media to generate its best optical property. Motorized jack (11) is provided for maintenance of a mechantronics device to keep lower chamber assembly down to replace optical media in the system. A Spectroscopic vision system (12) is a optical vision system with multiple optical components with mechanical stricture to get spectral images of hyper spectral spectroscopic system. It is the optical system which has higher depth to filed and parallel vision property for real information capture.

Spectroscopic sensor (13) is a photo electric sensor or CMOS or CCD sensor which can convert photonics light information to electric form to image processing analysis and optical coherent tomography. Multispectral phonics source or Laser source (14) is a photonics light source which is in NIR spectral range with collimated light out put with Top Hat profile as a system component of hyper spectral spectroscopy and optical coherent tomography. It can be a NIR laser source with collimated optics for collimated beam radiation. Intelligent viscosity sensor (15) is a software sensor which coupled with spectroscopic sensor to get information of viscosity of optical media.

Intelligent refractive index sensor (16) is a sensor which developed from software and light collimation travel to get optical properties of optical media. A multi component system (17) which developed from point no 10 and 12 to 16 points. Intelligent refractive index sensor (18) is a intelligent software analysis and processing with reference to different wavelengths effect on gemstone. Close loop control system for optical media (19) is a system which can control the properties of optical media as per suitability of gemstone by controlling temperature, viscosity and absence of air. Optical media for spectroscopy (20) is a high density media which optical properties will change with reference to temperature and outer atmospheric effect. It can be a metal and its solid state will convert in dense liquid media. Motion and optical media control system (21) is a electro mechanical and scientific system which can execute total automation system to support hyper spectral spectroscopy and optical coherent tomography. Diamond die placing position (22) is position of automation system at exit tray will install. Exit tray (23) is a mechanical device/fixture applicable to set diamond holding die with gemstone after evaluation in hyper spectral spectroscopic system.

One important aspect of embodiments of present invention relates to a best mathematical method with algorithm to make a decision of best possibilities of sawing planes in a 3D solid image of rough diamond to get maximum possible gain.

In a detail explanation of embodiment of invention, to scan the rough diamond to get total external surface geometry and information. The next process to mark some references to match at the time of internal structure close loop scanning system.

Hyper Spectral Spectroscopy of rough diamond (gemstone) in suitable very precise optical medium with spectroscopic vision system and tunable spectroscopic light source is a key embodiment of invention.

In a supreme embodiment of invention, hyper spectral spectroscopy with close loop scientific control system—development process of precise optical medium in best suitable environment which can match with phase velocity and optical properties of diamond.

Spectroscopic vision system is a telescopic optical system designed and integrated from high transmission in applicable near Infra Red (IR) wavelength optics and high resolution photoelectric Near-infrared spectroscopy (NIRS) sensor.

Wavelength tunable spectroscopic light source/narrow band collimated source/narrow band fine tuned laser is basically Visible and NIR photonics source designed and integrated from advanced NIR collimator optics and wavelength optics. It can be controlled and tuned by close loop control system to achieve exact matching of phase velocity, wavelength transmission and optical properties of diamond and optical media.

Development process of precise optical medium is scientific process to prepare high refractive index media in absence of oxygen and presence of noble gas by heating Selenium. The tuning of temperature and wavelength are important aspects of advanced feedback related close loop system to match phase velocity and refractive index of optical media and diamond.

The light transmission from clear portion of diamond and absorption from inclusions portions of diamond is key feedback for close loop system in this hyper spectroscopic mechanism.

In a key embodiment of application oriented innovation, Photonics radiation based temperature control system—a scientific method of photonic energy absorption and conversion in heat to increase temperature and its control mechanism. This close loop system is to develop optical media of spectroscopy and to keep optical properties as it is for long time.

The tunable photonics source/narrow band collimated source/laser can be controlled and illuminates in between wavelength band 350 nm to 2800 nm.

At the scanning process of the total system, diamond (gemstone) is completely surrounded by developed optical media to detect precise location of inclusions.

Integration of Optical Coherent Tomography (OCT) in combination with Hyper Spectral Spectroscopy—a method to get more information of rough diamond (gemstone) in image format with reference to different applicable wavelengths and image processing on multiple images to create detailed final internal structure of rough diamond (gemstone).

Key embodiment of system, Industrial Automation System for total related process. This system contains stirring, ultrasonic surface treatment with cleaning, drying with hot clean air, store in positional stand rack, pick up holding part with diamond, execution of scanning in hyper spectral spectroscopy system and placing in stand rack. Present system relates to precise motion control mechanism, pick and place mechanism with preprogrammed sequence to provide better safety and reliability with great efficiency and manless operation While, the invention has been described with respect to the given embodiment, it will be appreciated that many variations, modifications and other applications of the invention may be made. However, it is to be expressly understood that such modifications and adaptations are within the scope of the present invention, as set forth in the following claims.

I claim:

1. A device for gemstone evolution, comprising:
an entry tray track;
an entry tray;
a pick position system;
a gemstone-holding die/fixture;
a pick assembly mechanism;
a rotation assembly for spectroscopic analysis;
a torque-sensing motor;
a die/fixture cleaning chamber;
an optical media development chamber;
a radiation heat source or optical laser source;
a motorized jack for maintenance;
a spectroscopic vision system;
a spectroscopic sensor;
a multispectral photonics source or laser source;
an intelligent viscosity sensor;
an intelligent refractive index sensor;
a hyper-spectral spectroscopic system;
an optical coherent tomography system;
a closed-loop control system for optical media;
an optical medium for spectroscopy;
a motion and optical media control system;
a gemstone die placing position; and
an exit tray;
wherein the entry tray contains the gemstone-holding die/fixture with the gemstone to be evaluated;
wherein the gemstone holding die/fixture is a mechanical device/fixture that holds the gemstone for evaluation in the hyper-spectral spectroscopic system;
wherein the pick position system is provided for automatic positioning at entry tray installation;
wherein the pick assembly mechanism is a mechatronics mechanism with automation that picks the die and takes a predefined position;
wherein the rotation assembly for spectroscopic analysis is a mechanism to rotate the gemstone-holding die/fixture for hyper-spectral spectroscopy and optical coherent tomography;
wherein the torque-sensing motor mechanism obtains information regarding the optical medium's present situation;
wherein the die/fixture cleaning chamber is a chamber in which neutral or nobel gas flows to clean the gemstone in absence of air molecules;
wherein the optical media development chamber is a chamber in which, in absence of air and in presence of neutral or nobel gas with a closed-loop temperature control mechanism, the optimum state of the optical medium is obtained for better performance of hyper-spectral spectroscopy and optical coherent tomography;
wherein the radiation heat source or optical laser source is an electro optical mechanism that heats the optical medium through radiation energy to obtain the best optical property of the optical medium;
wherein the motorized jack is a mechantronics device for lowering the chamber assembly to replace the optical medium in the system for maintenance;
wherein the spectroscopic vision system is an optical vision system with multiple optical components with mechanical structure for obtaining spectral images of the hyper-spectral spectroscopic system, which is an optical system having higher depth of field and parallel vision properties for real information capture;
wherein the spectroscopic sensor is a photo electric sensor, complementary metal-oxide-semiconductor (CMOS) sensor, or charge coupled device (CCD) sensor, which coverts photonics light information to electric form for image processing analysis and optical coherent tomography;
wherein the multispectral phonics source or laser source is a photonics light source, which is in the near-infrared (NIR) spectral range with collimated light output with a Top Hat profile as a system component of hyper-spectral spectroscopy and optical coherent tomography;
wherein the intelligent viscosity sensor couples with the spectroscopic sensor to obtain information regarding viscosity of the optical medium;
wherein the intelligent refractive index sensor is a sensor which utilizes light collimation travel to obtain optical properties of the optical medium;
wherein the hyper-spectral spectroscopic system is a multi-component system utilizing the radiation heat source or photonics laser source, the spectroscopic vision system, and the intelligent refractive index sensor;
wherein the optical coherent tomography system analyzes and processes effects of different wavelengths on the gemstone;
wherein the closed-loop control system for optical media controls properties of the optical medium suitable for the gemstone by controlling temperature and viscosity in the absence of air;
wherein the optical medium for spectroscopy is a high-density optical medium having optical properties that change with reference to temperature and outer atmospheric effects;
wherein the motion and optical media control system is an electro mechanical system for executing total automation to support hyper-spectral spectroscopy and optical coherent tomography;
wherein the gemstone die placing position is the position the automation system installs at the exit tray; and
wherein the exit tray is a mechanical device/fixture that sets the gemstone-holding die/fixture with the gemstone after evaluation in the hyper-spectral spectroscopic system.

2. The device for gemstone evolution as claimed in claim 1, wherein the gemstone is a rough gemstone, and the hyper-spectral spectroscopy system is applied on the rough gemstone in the high-density optical medium with the spectroscopic vision system and a tunable spectroscopic light source.

3. The device for gemstone evolution as claimed in claim 1, wherein the rough gemstone is scanned to get the total external surface geometry.

4. The device for gemstone evolution as claimed in claim 1, wherein impurities are marked with an internal structure closed-loop scanning system.

5. The device for gemstone evolution as claimed in claim 1, wherein the spectroscopic vision system is a telescopic optical system designed and integrated for high transmission in applicable NIR wavelength regimes and a high resolution photoelectric NIR spectroscopy (NIRS) sensor.

6. The device for gemstone evolution as claimed in claim 1, wherein the multispectral photonics source or laser source is a tunable photonics source/narrow band collimated source or narrow band laser source that can be controlled and illuminated in a wavelength band of 350 nm to 2800 nm.

7. The device for gemstone evolution as claimed in claim 1, wherein Integration of Optical Coherent Tomography (OCT) in combination with Hyper Spectral Spectroscopy provides information of the rough gemstone in image format with reference to different applicable wavelengths and image processing on multiple images to create a detailed final internal structure of the rough gemstone.

8. The device for gemstone evolution as claimed in claim 1, wherein the closed-loop temperature control mechanism is a photonics radiation-based closed-loop temperature control mechanism that controls the optical energy absorption and conversion into heat utilizing the laser source to increase temperature of the optical medium.

9. The device for gemstone evolution as claimed in claim 8, wherein the wavelength of the laser source is in a range of 350 to 2800 nm.

10. The device for gemstone evolution as claimed in claim 8, wherein the photonics radiation-based closed-loop temperature control mechanism controls radiation energy and develops the optical media of spectroscopy to maintain the optical properties for an extended period of time.

11. The device for gemstone evolution as claimed in claim 1, wherein the device stirs, performs ultrasonic surface treatment and cleaning, dries with hot clean air, stores the gemstone in a positional stand rack, picks up the gemstone-holding die/fixture with the gemstone, scans the gemstone in the hyper-spectral spectroscopic system, and places the gemstone in the stand rack.

12. The device for gemstone evolution as claimed in claim 1, wherein a feedback control technique and image processing algorithm are used by the closed-loop control system to gather information related to torque, viscosity, and optical properties of the optical medium.

* * * * *